United States Patent
Moore et al.

(10) Patent No.: US 8,980,123 B2
(45) Date of Patent: Mar. 17, 2015

(54) TAGGED SCALE INHIBITOR COMPOSITIONS AND METHODS OF INHIBITING SCALE

(71) Applicants: Lucas Moore, Atlanta, GA (US); Laura Clapp, Atlanta, GA (US)

(72) Inventors: Lucas Moore, Atlanta, GA (US); Laura Clapp, Atlanta, GA (US)

(73) Assignee: Kemira Chemicals Inc., Kennesaw, GA (US)

( * ) Notice: Subject to any disclaimer, the term of this patent is extended or adjusted under 35 U.S.C. 154(b) by 0 days.

(21) Appl. No.: 13/867,506

(22) Filed: Apr. 22, 2013

(65) Prior Publication Data

US 2013/0234063 A1     Sep. 12, 2013

Related U.S. Application Data

(63) Continuation of application No. 12/849,544, filed on Aug. 3, 2010.

(51) Int. Cl.
| | | |
|---|---|---|
| *C09K 8/528* | (2006.01) | |
| *E21B 37/06* | (2006.01) | |
| *G01N 21/64* | (2006.01) | |
| *C02F 5/00* | (2006.01) | |
| *C02F 5/12* | (2006.01) | |
| *C02F 5/14* | (2006.01) | |

(52) U.S. Cl.
CPC ... *C02F 5/00* (2013.01); *C02F 5/12* (2013.01); *C02F 5/14* (2013.01); *C09K 8/528* (2013.01); *E21B 37/06* (2013.01); *G01N 21/64* (2013.01)
USPC ...................................... 252/180; 250/459.1

(58) Field of Classification Search
CPC ......... C09K 8/528; E21B 37/06; G01N 21/64
USPC ....................................... 252/180; 250/459.1
See application file for complete search history.

(56) References Cited

U.S. PATENT DOCUMENTS

| | | |
|---|---|---|
| 3,634,366 A | 1/1972 | Chujo et al. |
| 3,907,572 A | 9/1975 | Ueda et al. |
| 5,232,603 A | 8/1993 | Denzinger et al. |
| 5,506,315 A | 4/1996 | Meyer et al. |
| 5,630,907 A | 5/1997 | Nilz et al. |
| 5,655,601 A | 8/1997 | Oddo et al. |
| 5,736,405 A | 4/1998 | Alfano et al. |
| 5,804,662 A | 9/1998 | Schade et al. |
| 6,312,644 B1 | 11/2001 | Moriarty et al. |
| 6,585,933 B1 | 7/2003 | Ehrhardt et al. |
| 7,703,516 B2 | 4/2010 | Hills et al. |
| 2004/0135125 A1* | 7/2004 | Morris et al. .............. 252/408.1 |
| 2005/0181380 A1* | 8/2005 | Isobe ................................ 435/6 |
| 2007/0267193 A1 | 11/2007 | Hills et al. |

FOREIGN PATENT DOCUMENTS

| | | |
|---|---|---|
| EP | 1639228 | 4/2008 |
| JP | 53025690 | 3/1978 |
| JP | 63059353 | 3/1988 |
| JP | 07228634 | 8/1995 |
| WO | WO 9830664 | 7/1998 |

OTHER PUBLICATIONS

Burr, B.J. et al., "The Development and Application of a Detectable Polymeric Scale Inhibitor to Control Sulfate Scales by Squeeze Applications", SPE 16261, Copyright 1987, Society of Petroleum Engineers, Paper prepared for presentation of the SPE International Symposium on Oilfield Chemistry, San Antonio, TX, Feb. 4-6, 1987, pp. 195-204.

Vetter, O.J., "The Chemical Squeeze Process—Some New Information on Some Old Misconceptions", SPE-AIME, Union Oil Co. of California, Journal of Petroleum Technology, Mar. 1973, pp. 339-353.

* cited by examiner

*Primary Examiner* — Kelechi Egwim

(74) *Attorney, Agent, or Firm* — King & Spalding

(57) ABSTRACT

Scale inhibitor compositions and methods of inhibiting scale formation generally include a tagged scale inhibiting (co) polymer including at least one scale inhibiting moiety and an imidazole moiety. The imidazole moiety fluoresces at a wavelength of about 424 nm and can be used to detect the amount of scale inhibitor present.

9 Claims, No Drawings

TAGGED SCALE INHIBITOR COMPOSITIONS AND METHODS OF INHIBITING SCALE

CROSS REFERENCE TO RELATED APPLICATION

This application is a continuation of U.S. patent application Ser. No. 12/849,544 filed Aug. 3, 2010. The complete disclosure of the above-identified application is fully incorporated herein by reference.

BACKGROUND

The present disclosure generally relates to tagged scale inhibition compositions and methods of inhibiting scale. More particularly, the present invention relates to imidazole tagged scale polymeric inhibitors for use in water treatment and/or oil field applications.

Scale inhibiting polymers are often used in water treatment and oil field applications to minimize and/or prevent scale deposition. The deposition of scale can occur in the transport of aqueous mixtures and in subterranean rock formations due to the presence of water bearing alkaline earth metal cations such as calcium, barium, strontium, and the like as well as the presence of anions such as phosphate, sulfates, carbonates, silicates and the like. When these ions are in sufficient concentrations, a precipitate can form that builds up on interior surfaces of the conduits used for transport or in the subterranean rock formations, which restrict flow of the media of interest, e.g., water or oil. In oilfield applications, scales that are commonly formed include calcium sulfate, barium sulfate, and/or calcium carbonate that are generally formed in the fresh waters or brines used in well stimulation and the like as a result of increased concentrations of these particular ions, the water pH, pressures, and temperatures. In addition, calcium phosphate can form from the phosphate chemistry that is commonly used to treat wells and pipes for corrosion. The buildup of these mineral precipitates can reduce or block flow in the conduits and rock formations as well as cause other problems. In many cases, the first warning of the existence of a significant scale deposit may be a decline in well performance. In these instances, scale removal techniques may become necessary. As a result, a potentially substantial cost including downtime is required lost to effect repair as a result of scaling.

Scale inhibiting materials are often added directly to a fluid to be treated or applied to oil bearing rock formations by means of "squeeze treatment". Squeeze treatment is a treatment used to control or prevent scale deposition in a rock formation. In the squeeze application, the scale inhibitor is pumped into a water-producing zone and attaches to the formation by chemical adsorption or by temperature-activated precipitation. When the well is put back into production, the scale inhibitor leaches out of the formation rock to treat the fluid. Some chemicals typically used in scale-inhibitor squeeze applications include phosphonated carboxylic acids or polymers.

Scale formation is only controlled if the scale inhibitor polymer is present at a treatment level equal to or above the product's defined minimum inhibitor concentration. When the scale inhibitor is below the minimum inhibitor concentration such as may occur during use, adsorption or degradation, additional amounts are then needed. For example, once the well is subjected to the squeeze application and the well is again operational, the concentration of the scale inhibitor in the produced fluids will diminish over time until such time that the scale inhibitor is at about or below the minimum inhibitor concentration. However, it is difficult to determine when more scale inhibitor is needed and in which conduit or well it is needed. To address this problem, scale inhibitors are often tagged or labeled so that the presence or absence of the scale inhibitor can be readily detected. Prior art scale inhibitors are generally tagged by introduction of specific atoms such as phosphorous, boron, and the like such that the concentration can be readily detected by inductively coupled plasma (ICP) analysis for the tagged atom. Alternatively, the scale inhibitor can be tagged fluorescent moieties. However these compounds are generally limited to structures that include one or more conjugated six member benzene rings that fluoresce at about 292 nm.

While the prior art fluorescent tagged scale inhibitors are suitable for their intended, there is a need in the art for additional fluorescent moieties that emit at different wavelengths, which would be beneficial in multi-tagged systems where multiple scale inhibitors with tags having different fluorescent wavelengths are utilized. Examples of such a system would be when more than one wells are drilled and the oil is collected from one central location. The multi-tagged system would allow the operators to know which specific wall requires more antiscalent, simply by looking at what frequency is missing.

BRIEF DESCRIPTION OF THE INVENTION

Disclosed herein are scale inhibition compositions and methods of inhibiting scale. In one embodiment, the scale inhibition (co)polymer includes at least one scale inhibiting polymerized monomer selected from the group consisting of acrylic acid; vinyl sulfonic acid or vinyl sulfonate salts; vinyl phosphoric acid or vinyl phosphonate salts; vinylidene diphosphonic acid or salts thereof; methacrylic acid; vinyl acetate; vinyl alcohol; vinyl chloride; unsaturated mono- or di-carboxylic acids or anhydrides; vinyl chloride; styrene-p-sulfonic acid, or styrene sulfonates salts; acrylamido-2-methylpropanesulfonic acid (AMPS); hydroxyphosphonoacetic acid (HPA); hypophosphorus acids acrylamides, propargyl alcohol having formula $HC{\equiv}C{-}CH_2{-}OH$; butyr-1,4-diol, and mixtures thereof; and a 1-vinyl imidazole polymerized monomer of the formula:

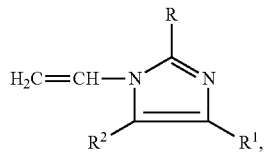

wherein R, $R_1$ and $R_2$ are the same or different, and each R, $R_1$, and $R_2$ is selected from the group consisting of H, an alkyl group, an aromatic group, a phosphate group, a nitrate group, and a sulfate group.

In another embodiment, a process for determining a concentration of a scale inhibiting (co)polymer for inhibiting scale formation comprises introducing an effective amount of the scale inhibition (co)polymer to an aqueous medium to inhibit calcium carbonate, calcium sulfate, barium sulfate, and/or calcium phosphate scale formation, wherein the scale inhibition (co)polymer includes at least one scale inhibiting moiety and an imidazole moiety formed by polymerizing at least one scale inhibiting monomer and a 1-vinylimidazole monomer; measuring a fluorescence signal corresponding to the imidazole moiety; and determining a concentration of the scale inhibiting (co)polymer based on the fluorescence signal.

In another embodiment, a water treatment solution for inhibiting scale formation comprises a scale inhibiting (co) polymer including an imidazole moiety, comprising at least one scale inhibiting polymerized monomer selected from the group consisting of acrylic acid; vinyl sulfonic acid or vinyl sulfonate salts; vinyl phosphoric acid or vinyl phosphonate salts; vinylidene diphosphonic acid or salts thereof; methacrylic acid; vinyl acetate; vinyl alcohol; vinyl chloride; unsaturated mono- or di-carboxylic acids or anhydrides; vinyl chloride; styrene-p-sulfonic acid, or styrene sulfonates salts; acrylamido-2-methylpropanesulfonic acid (AMPS); hydroxyphosphonoacetic acid (HPA); hypophosphorus acids acrylamides, propargyl alcohol having formula HC≡C—CH$_2$—OH; butyr-1,4-diol, and mixtures thereof; and a 1-vinyl imidazole polymerized monomer of the formula:

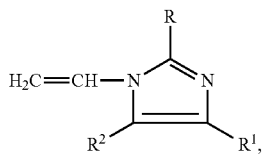

wherein R, R$_1$ and R$_2$ are the same or different, and each R, R$_1$, and R$_2$ is selected from the group consisting of H, an alkyl, an aromatic, phosphate, nitrate, and sulfate; and a solvent.

The disclosure may be understood more readily by reference to the following detailed description of the various features of the disclosure and the examples included therein.

DETAILED DESCRIPTION

The present disclosure is generally directed to scale inhibiting compositions and methods for inhibiting scale formation. The compositions generally include a scale inhibiting (co)polymer including an imidazole moiety, wherein the fluorescence of the imidazole moiety can be used to determine the concentration of the scale inhibiting (co)polymer. As used herein, the term (co)polymer is generally defined as materials that are produced by polymerization of more than one type of monomer (including 2, 3, 4, or more different monomers) without restriction on the number of monomer units that are incorporated into the product provided that at least one of the monomers is a scale inhibiting moiety and at least one of the monomers is an imidazole moiety. The imidazole moiety, without substitution, fluoresces at about 424 nanometers (nm), thereby providing the scale inhibitor (co) polymer with a means for monitoring the concentration of the scale inhibitor (co)polymer at a wavelength different from prior art's monitoring of specific atoms or scale inhibiting polymers tagged with one or more aromatic benzene rings. Because of the difference in wavelength, the scale inhibiting (co)polymer including the imidazole moiety can be used in multi-tagged systems.

Scale inhibiting (co)polymers including the imidazole moiety are obtainable by free radical polymerization of one or more scale inhibiting monomers with a 1-vinylimidiazole monomer of the formula (1):

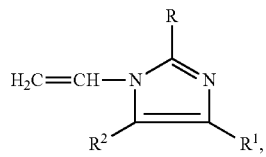

wherein R, R$_1$ and R$_2$ are the same or different, and each can be H, an alkyl, or an aromatic group. In some embodiments, R, R$_1$ and R$_2$ may include inorganic functionality, such as: phosphates, nitrates, or sulfates. As will be appreciated by those skilled in the art, the substituent can be used to shift the maximum wavelength fluorescence emission. When R, R$_1$ and R$_2$ are H, the imidazole moiety fluoresces at about 424 nm.

Suitable scale inhibiting monomers include, without limitation, acrylic acid; vinyl sulfonic acid or vinyl sulfonate salts; vinyl phosphoric acid or vinyl phosphonate salts; vinylidene diphosphonic acid or salts thereof; methacrylic acid; vinyl acetate; vinyl alcohol; vinyl chloride; unsaturated mono- or di-carboxylic acids or anhydrides, such as maleic anhydride, maleic acid, fumaric acid, itaconic acid, aconitic acid, mesaconic acid, citraconic acid, crotonic acid isocrotonic acid, angelic acid, tiglic acid; vinyl chloride; styrene-p-sulfonic acid, or styrene sulfonates salts; allyl sulfonate salts; acrylamido-2-methylpropanesulfonic acid (AMPS); hydroxyphosphonoacetic acid (HPA); hypophosphorus acids such as H$_3$PO$_3$, giving units of formula —PO(OH)—; acrylamides, propargyl alcohol having formula H≡C—CH$_2$—OH; butyr-1,4-diol, hydroxyethylmethacrylate (HEMA), hydroxyethylacrylate (HEA) and mixtures thereof.

While the above-mentioned scale inhibiting monomers are usually comprised in the polymer backbone, other monomers and/or other groups may also be included. For example, the other groups can result from a polymerization initiator or can be end-capping groups.

The polymerization of the monomers can be carried out in the presence of polymerization initiators including, without limitation, ammonium persulfate, sodium persulfate, Vazo initiators, AIBN, organic or inorganic peroxides, cerium ammonium nitrate, perchlorates, and the like. The polymerization initiators are generally in an amount of about 0.01 to about 3 weight percent based on the total weight of the monomers.

Any polymerization method can be used to prepare the polymers. Free-radical polymerization methods are generally preferred. Suitable methods include aqueous bulk/dispersion polymerization, solution polymerization, or emulsion polymerization. Preferably, the polymerization process is solution polymerization, wherein water is charged to a reaction vessel fitted with a mechanical stirrer and water condenser and heated to a temperature within a range of 45 to 110° C. One or more polymerization initiators may be added or these may be fed in later. The 1-vinylimidazole monomer may also be added to this charge, added to the polymer feed or fed in separately. A monomer feed(s), soluble initiator feed and optionally a chain transfer reagent feed are added to the vessel over a period of time.

The imidazole moiety in the scale inhibiting (co)polymer is generally at a molar amount of less than 20% by monomer. In other embodiments, the imidazole moiety is at a weight percent of total monomer of 10% to 20%; and in still other embodiments, the imidazole moiety is at a weight percent of 2 to 10%.

The scale inhibiting (co)polymer has a weight average molecular weight of 1200 to 15000 Daltons; in other embodiments, the weight average molecular weight is 4000 to 10000 Daltons, and in still other embodiments, the weight average molecular weight is 1500 to 3000 Daltons.

The scale inhibitor polymer including the imidazole moiety can be detected by fluorometry, for example using a fixed wavelength fluorometer.

The scale inhibiting (co)polymer can be used as a scale inhibitor in any industrial water system where a scale inhibitor is needed. Suitable industrial water systems, include, without limitation, cooling tower water systems (including open recirculating, closed and once-through systems); petroleum wells, downhole formations, geothermal wells and other oil field applications; boilers and boiler water systems; mineral process waters including mineral washing, flotation and benefaction; paper mill digesters, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurization water; water reclamation and purification systems; membrane filtration water systems; food processing streams (meat, vegetable, sugar beets, sugar cane, grain, poultry, fruit and soybean); and waste treatment systems as well as in clarifiers, liquid-solid applications, municipal sewage treatment and industrial or municipal water systems.

This effective amount of the scale inhibitor (co)polymer will generally vary depending on the particular system to be treated and scale inhibiting moieties in the scale inhibiting (co)polymer and will be influenced by factors such as the area subject to deposition, pH, temperature, water quantity, and the respective concentration in the water of the potential scale and deposit forming species. For the most part, the treatment solution according to the present disclosure will be effective when the scale (co)polymer used at levels less than 35 parts per million. In some embodiments, the composition is effective at concentrations of about 4 to about 7 parts per million and in still other embodiments; the effective concentration is about 0.5 to about 3 parts per million. The composition can be added directly into the desired aqueous system to be treated in a fixed quantity or can be provided as an aqueous solution and added continuously or intermittently to the aqueous system as can be desired for some applications.

By way of example, the compositions of the scale inhibitor (co)polymer can be suitably used in oilfield injection and production waters, including topside, downhole and rock formation squeeze applications at the well site. In oilfield injection and production waters, scale formation can constrict injection lines, flow lines, and tubing strings. Without being limited by theory, the above noted composition functions by modifying the crystal growth of nucleating scale particles and interrupting and delaying crystal growth. They also sequester metal ions, making them unavailable for ion pairing with anions and hence preventing precipitation of insoluble scale.

In one embodiment, the scale inhibiting (co)polymer composition is utilized in a squeeze application. The scale inhibiting (co)polymer is diluted in a suitable carrier solvent (usually brine) and propagated out to an optimized radial distance into the oil producing formation, where it is retained and then released slowly back into the aqueous phase during normal well production. In one embodiment, the squeeze process generally includes applying a dilute solution of the scale inhibiting (co)polymer with surfactant (0.1%) to clean and cool the near wellbore. Once cleaned, a high concentration solution of the scale inhibiting (co)polymer at between 5 and 20% is introduced, followed by a low concentration solution of the scale inhibiting (co)polymer. The solutions are left in contact with the reservoir for a period of time effective to allow for adsorption equilibration, after which the well is returned to production. Adhesion to the formation allows the scale inhibiting (co)polymer to remain within the near-wellbore area without being pumped up in the oil/water emulsion. Although squeeze application of the chemical is the most common method of treating downhole scale, the product could also be applied by other techniques commonly used offshore, which include gas-lift injection, downhole annulus injection, encapsulation or soluble matrix techniques, subsea wellhead injection via umbilical or indeed secondary topside treatments to enhance inhibitor performance as process conditions vary scaling tendency.

Prior to application of the product, experiments can be conducted in a laboratory to determine an effective minimum inhibitor concentration (MIC) which just inhibits inorganic scale formation under simulated production conditions. The ability of the operator to quickly and accurately determine the amount of scale inhibitor in the produced fluids and compare this to the MIC values generated allows him to decide when it is most suitable to retreat the reservoir or increase the topside addition rate to ensure that no damage occurs to his reservoir or equipment due to inorganic scale deposition.

The following examples are presented for illustrative purposes only, and are not intended to be limiting.

EXAMPLES

In the following examples, maleic anhydride, vinyl imidazole and ethylenediamine tetraacetic acid were obtained from Sigma-Aldrich Co. Sodium allyl sulfonate was obtained from McGean Rohco, Inc Ammonium persulfate was obtained from Kemira Chemicals, Inc.

Example 1

In this example, sodium allyl sulfonate was tagged with 10% vinyl imidazole (SASMAC/10% IM). Sodium allyl sulfonate (340.10 g, maleic anhydride (27.84 g) vinyl imidazole (15.10 g) and EDTA (4.72 g) were charged to a reactor. The reactor was equipped with a Teflon coated thermocouple, a nitrogen inlet, one feeding tube inlet, a glass and Teflon stir shaft, and a heating mantle. The reaction was carried out at 90° C. with constant flow of nitrogen and low agitation. One feeding tank containing ammonium persulfate (6.96 g) in water (32.0 g) was prepared and fed into the reactor over a two hour period. Maleic anhydride (27.84 g) was fed manually over the 2 hour initiator period. Once the initiator and maleic anhydride feeds were complete, the reaction was held at 90° C. for one hour before cooling to room temperature.

Example 2

In this example, sodium allyl sulfonate was tagged with 5% vinyl imidazole (SASMAC/5% IM). Sodium allyl sulfonate (340.10 g, maleic anhydride (27.84 g) vinyl imidazole (7.55 g) and EDTA (4.72 g) were charged to a reactor and reacted in accordance with Example 1. Once the initiator and maleic anhydride feeds were complete, the feed line was flushed with water (5 g) and the reaction was held at 90° C. for one hour before cooling to room temperature.

Example 3

In this example, polyacrylate was tagged with varying amounts of vinyl imidazole (AA/IM) having a molecular weight of about 2,000 Daltons. The reactor was equipped with a Teflon coated thermocouple, a nitrogen inlet, three feeding tube inlets, a stainless steel stir shaft, and a heating mantle. Water (190.7 g) was charged to the reactor and heated to 85° C. The reaction was carried out at 85° C. with constant flow of nitrogen and low agitation.

Acrylic Acid/2% Imidazole (AA/2% IM)
Feed Tank 1: glacial acrylic acid (279.7 g), vinyl imidazole (5.71 g)
Feed Tank 2: water (89.5 g), sodium persulfate (12.7 g)
Feed Tank 3: water (44.8 g), sodium bisulfite (161.0 g)
Acrylic Acid/5% Imidazole (AA/5% IM)
Feed Tank 1: glacial acrylic acid (271.2 g), vinyl imidazole (14.2 g)
Feed Tank 2: water (89.5 g), sodium persulfate (12.7 g)
Feed Tank 3: water (44.8 g), sodium bisulfite (161.0 g)
Acrylic Acid/10% Imidazole (AA/10% IM)
Feed Tank 1: glacial acrylic acid (256.9 g), vinyl imidazole (28.5 g)
Feed Tank 2: water (89.5 g), sodium persulfate (12.7 g)
Feed Tank 3: water (44.8 g), sodium bisulfite (161.0 g)
Acrylic Acid/20% Imidazole (AA/20% IM)
Feed Tank 1: glacial acrylic acid (228.5 g), vinyl imidazole (57.0 g)
Feed Tank 2: water (89.5 g), sodium persulfate (12.7 g)
Feed Tank 3: water (44.8 g), sodium bisulfite (161.0 g)

Each reagent mixture was fed into a reactor over a four hour period. Once the feeds were complete, the feed lines were flushed with water (10.0 g) and the reaction mixture held at 85° C. for one hour before cooling to room temperature. The pH was adjusted to 6.5 using 50% sodium hydroxide.

Table 1 provides the flurescence intensities at 424 nm at different levels of concentration for the various (co)polymers.

| Polymer | Mw | IM (%) | $CaCO_3$ | $BaSO_4$ | Intensity (0.85 ppm) | Intensity (3.4 ppm) | Intensity (34 ppm) |
|---|---|---|---|---|---|---|---|
| SASMAC/IM | | 10 | — | 3.6 | 14.39 | 18.905 | 133.18 |
| SASMAC/IM | | 5 | — | 3.6 | 9.81 | 25.048 | 99.319 |
| AA/IM | 3328 | 2 | 2.4 | 5 | — | 7.007 | 20.86 |
| AA/IM | 3279 | 5 | 2.7 | 5 | — | 10.199 | 32.92 |
| AA/IM | 2902 | 10 | 2.4 | 5 | — | 19.92 | 33.96 |
| AA/IM | 3003 | 20 | 2.4 | 5 | — | 17.54 | 64.76 |
| AA/IM | 1924 | 2 | 2 | 6.4 | — | 6.24 | 15.68 |
| AA/IM | 1800 | 5 | Not complete | 5.5 | — | 7.85 | 26.51 |
| AA/IM | 1436 | 10 | 2 ppm = 91% | 5.5 | — | 13.764 | 26.25 |
| AA/IM | 1469 | 20 | Not complete | Not complete | — | 6.54 | 58.76 |

The data shows that the vinylimidazole moiety in the scale inhibiting (co)polymers provided an effective amount of fluorescence at about 424 nm for the different amounts of scale inhibitor present. The fluorescence emission signal at about 424 nm makes the scale inhibitor (co)polymer suitable for use in multi-tagged systems. For example, the scale inhibiting (co)polymer with the imidazole moiety can be used with a sodium styrene sulfonate inhibitor, which by itself fluoresces at 292 nm The imidazole (co)polymers provide scale inhibition properties provide the ability to monitor scale inhibitor levels during the oil or mining applications, among others.

This written description uses examples to disclose the invention, including the best mode, and also to enable any person skilled in the art to make and use the invention. The patentable scope of the invention is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A process for determining a concentration of a scale inhibiting (co)polymer for inhibiting scale formation, the process comprising:
   introducing an effective amount of the scale inhibiting (co)polymer to an aqueous medium to inhibit calcium carbonate, calcium sulfate, barium sulfate, and/or calcium phosphate scale formation, wherein the scale inhibiting (co)polymer includes at least one scale inhibiting moiety and an imidazole moiety formed by polymerizing at least one scale inhibiting monomer and a 1-vinylimidazole monomer;
   measuring a fluorescence signal corresponding to the imidazole moiety; and
   determining a concentration of the scale inhibiting (co) polymer based on the fluorescence signal.

2. The process of claim 1, wherein the at least one scale inhibiting monomer is selected from the group consisting of acrylic acid; vinyl sulfonic acid or vinyl sulfonate salts; vinyl phosphoric acid or vinyl phosphonate salts; vinylidene diphosphonic acid or salts thereof; methacrylic acid; vinyl acetate; vinyl alcohol; vinyl chloride; unsaturated mono- or di-carboxylic acids or anhydrides; vinyl chloride; styrene-p-sulfonic acid, or styrene sulfonates salts; acrylamido-2-methylpropanesulfonic acid (AMPS); hydroxyphosphonoacetic acid (HPA); hypophosphorus acids acrylamides, propargyl alcohol having formula $HC{\equiv}C{-}CH_2{-}OH$; butyr-1,4-diol, and mixtures thereof.

3. The process of claim 1, wherein the at least one scale inhibiting monomer is acrylic acid.

4. The process of claim 1, wherein the scale inhibiting (co)polymer comprises a sodium allyl sulfonate monomer and an acrylic acid monomer.

5. The process of claim 1, wherein the imidazole moiety is at a wt% of total monomer of 2 to 20, wt% of the scale inhibiting (co)polymer.

6. The process of claim 1, wherein the average molecular weight is 2000 to 3500 Daltons.

7. The process of claim 1, wherein the effective amount is less than 35 parts per million.

8. The process of claim 1, wherein the effective amount is 0.5 to 35 parts per million.

9. The process of claim 1, wherein the process is a squeeze application.

* * * * *